United States Patent [19]

Strippgen

[11] Patent Number: 5,261,303
[45] Date of Patent: Nov. 16, 1993

[54] ROD CUTTER

[76] Inventor: Walter E. Strippgen, 4960 McIntyre, Golden, Colo. 80403

[21] Appl. No.: 855,299

[22] Filed: Mar. 23, 1992

[51] Int. Cl.⁵ .............................................. B26D 3/16
[52] U.S. Cl. ........................................ 83/199; 16/324; 16/335; 83/200
[58] Field of Search ................ 83/199, 200, 694, 634; 30/94, 95, 93; 16/113, 115, 324, 335

[56] References Cited

U.S. PATENT DOCUMENTS

| | | | |
|---|---|---|---|
| 54,520 | 5/1866 | Flinn | 30/226 |
| 146,846 | 1/1874 | Stevens | 83/200 |
| 260,173 | 6/1882 | Durfee | 83/199 |
| 327,610 | 10/1885 | Stackpole | 83/199 |
| 434,597 | 8/1890 | Hay | 83/199 |
| 464,976 | 12/1891 | Lindfors | 83/200 |
| 1,822,947 | 9/1931 | White | 16/335 X |
| 2,249,515 | 7/1941 | Carroll | 30/226 |
| 2,494,996 | 1/1950 | Geddes | 30/226 |
| 2,543,018 | 2/1951 | Hainline | 30/131 |
| 2,560,318 | 7/1951 | Wenger | 30/226 |
| 2,617,670 | 11/1952 | Welsh | 16/324 X |
| 3,315,669 | 4/1967 | Rhodes | 83/200 X |
| 3,333,338 | 8/1967 | Burns | 30/233 |
| 3,370,353 | 2/1968 | Weissman et al. | 30/233 |
| 3,494,233 | 2/1970 | Kojima | 83/199 |
| 4,003,279 | 1/1977 | Carmichael et al. | 83/199 |
| 4,722,257 | 2/1988 | Deon et al. | 83/605 |

*Primary Examiner*—Frank T. Yost
*Assistant Examiner*—Raymond D. Woods

[57] ABSTRACT

A base carries a tool head having two bore containing members that are relatively rotatable with respect to each other on a common axis of rotation. The bore portions contained in the two members are offset from the common axis of rotation by no more than one bore diameter. The two portions of the bore align in one relative position of rotation, but a handle is connected to at least one member to move at least that member to a position in which the bore portions are partially misaligned, severing any rod placed in the common bore by a combination of offset shearing action and rotary wringing action.

4 Claims, 1 Drawing Sheet

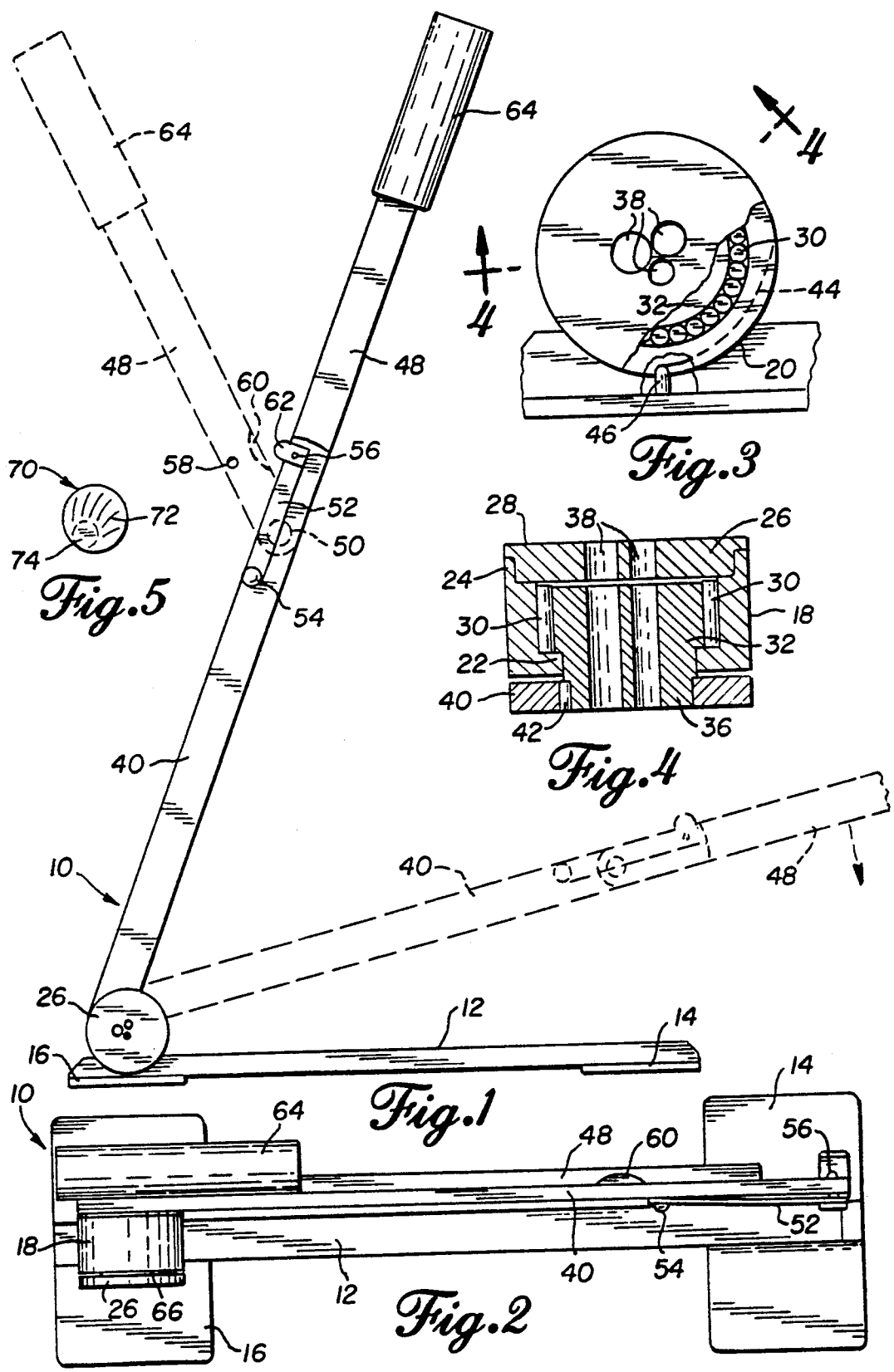

ROD CUTTER

TECHNICAL FIELD

The invention generally relates to cutlery and more specifically relates to pipe and rod cutters, especially rotary cutters having a pivoted lever mounted thereon, external rotary cutters, and pipe or rod encircling external rotary cutters. In addition, the invention specifically relates to cutting tools with plural cooperating blades, especially shears with plural cooperating blades with a guard, guide, or gauge; multiplex shears; multiplex shears with blade moving means; and rotary blade shears including those with reciprocating blade.

BACKGROUND ART

The art of rod cutting has produced both hand held and bench mounted tools. These tools are capable of cutting a wide variety of rod strengths and thicknesses, ranging from wire to hardened steel rod. Thus, a tool can be made to cut almost any workpiece. However, the quality of the cut and the characteristics of the tool are subject to wide variation. An area having extremely difficult requirements is surgery. Here, the tool must be made with sufficient clearances to permit sterilization, but the workpiece frequently is extremely tough surgical steel. In addition, the accuracy requirement may be extremely rigid, as the rod being cut is being custom fitted into a patient in the normal course of a surgical procedure.

According to present practice in the art, surgeons have employed the well known bolt cutter having compound levers and pivoted jaws, which has a combination of strength, mechanical advantage, and looseness of parts to permit its use in an operating room. This tool also has several notable disadvantages. A very notable one is that a bolt cutter leaves the cut end of a cut rod with a rough, wedge shaped tip, which is very undesirable as a long term fixture in the human body. Further, due to the extreme hardness of some surgical steel rods, the bolt cutter can be extremely difficult to use and may lead to muscle damage and hernia in the user. Still another problem is that a bolt cutter snaps off the end of the workpiece, which has been known to fly through the air with considerable force and cause damage.

Among other known designs for rod or bolt cutters is the teachings of U.S. Pat. No. 54,520, wherein a tool housing carries both a cap plate and an opposed cutter disk with matching bores located over the faces of the disc and cap plate, but generally around the circumferential area. A wire or rod is inserted through the common bores and the cutter disk is rotated with respect to the cap plate in order to cut the workpiece. An advantage of this arrangement is that there is no center pin on which the plates rotate. Thus, the size of rod that the cutter can sever is not limited by the size of a center pin, which would be in danger of breaking before such large rod is cut. However, it is notable that the matching bores are considerably offset radially outwardly from the typical location for a center pin, if such were to be present.

Another cutter is shown in U.S. Pat. No. 2,560,318 wherein a tool has multiple holes to allow different gage wire or bolts to be cut in a pivoting cutting action about a center pin. The holes typically are offset by a considerable radial distance from the center pin. Other tools having a center pivot pin are shown in U.S. Pat. Nos. 2,494,996, 3,333,338, and 3,370,353. In these, also, the cutting holes are radially spaced from the center pin by a substantial distance. In addition, the tools of the latter three patents appear to be hand held tools that are portable enough to be placed in a sterilizer.

Further examples of the state of the art appear in U.S. Pat. No. 2,249,515, which discloses a simple pivoted shear; U.S. Pat. No. 2,543,018, which discloses a combination of a disk with rod supporting holes and a cutting blade that operates against the disk; and U.S. Pat. No. 4,722,257, which discloses bench mounted bolt cutter. These tools employ scissors style shearing action, in which the work site is in progressive motion along the closing blades.

It would be desirable to have a rod cutter that is adapted to the specific requirements of an operating room where, as noted above, the workpiece rods are of especially hard steel. Also, it would be desirable to have a rod cutter that operates by shearing action with an applied rotary torque or wringing action, so that the surgical steel rods are sheared with added ease and with an excellent smoothness on the cut end. A bench mounted cutter could offer still better ease of use and less chance of injury to the user, but any cutter of bench size would have to be of a size to accommodate sterilization requirements. Further, the construction of the rod cutter should permit space to be left between moving parts so that all parts can be sterilized.

To achieve the foregoing and other objects and in accordance with the purpose of the present invention, as embodied and broadly described herein, the rod cutter of this invention may comprise the following.

DISCLOSURE OF INVENTION

Against the described background, it is therefore a general object of the invention to provide an improved surgical rod cutter that is capable of cutting, typically, surgical 316-L implant rod. While the cutting of this rod is a difficult task, the invention has as a further object that such rod be cut while using relatively low applied force and that the quality of the cut be extremely high, with a smooth, burr free end.

Another object is that the rod cutter be adapted to fit into conventional hospital sterilization equipment. In combination with the foregoing objects relating to ease of use and high quality cut, the requirement of compact size creates a substantial challenge.

An important object is to provide a rod cutter that leaves a burr free end on the severed rod, so that the rod is especially suited for use in surgery.

A related object is to provide in a rotary action rod cutter tool a cutting bore that is located as close as possible to the center of rotary or pivotal action, while still applying a shearing force to the workpiece. It is desired that each cutting bore be located within one diameter of the pivot axis of the tool head, so that the workpiece is subjected to a combination of shearing forces and wringing forces.

Still another object is that the rod cutter operate over a limited arc of handle movement. In order to allow the operator to apply his body weight to operation of a cutter, the arc of handle movement should be less than 90° and is preferred to be no more than about 70°.

An important object is to create a rod cutter that will retain both ends of the rod even after cutting is complete. Retaining rod ends eliminates the danger to surrounding people and equipment of damage from flying scraps.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a rod cutter includes a base supporting the cutter against an underlying surface. A tool head is carried on the base for shearing a rod when the tool head is operated. The tool head includes a body housing an inner chamber. A first bore defining member is connected to the body and maintained in relatively fixed position with respect to the body. A second bore defining member is carried at least partially within the inner chamber and is supported by the body for relative rotation with respect to the first bore defining member. The first and second bore defining members mutually define at least one common bore extending longitudinally parallel to an axis of rotation between the first and second members and laterally offset from this axis. First and second bore portions are located, respectively, in each of members in a position laterally offset from the axis of rotation by no more than one diameter of the bore. These first and second bore portions are coaxially alignable when the first and second bore defining members are in a first predetermined relative position of rotation. A handle operates the tool head by moving relatively to the base means. This handle is connected to the second bore defining member and rotatably moves the second bore defining member with respect to the first bore defining member between at least the first predetermined position and a second position in which the two bore portions are at least partially axially misaligned. In use, this motion severs a rod held in the bore.

According to another aspect of the invention, a rod cutter provides a base for supporting the cutter against an underlying surface. A tool head for shearing a rod when said tool head is operated includes a hollow cylindrical body having a central axis. An end cap closes one end of the body and is maintained in a relatively fixed position with respect to the body. A core is carried at least partially within the body for rotation on the axis of the cylinder, and an annular bearing is carried between the inside surface of the body and the outside circumferential surface of the core for supporting the core for rotation with respect to the end cap. The core and end cap mutually define at least one bore having first and second portions located, respectively, in the core and in the end cap, wherein both portions are in a position laterally offset from the axis of the body. The first and second bore portions are coaxially alignable when the core and end cap are in a first predetermined relative position of rotation. A handle operates the tool head by moving relatively to the base. The handle is connected to the core and rotatably moves the core with respect to the end cap between at least the first position and a second position in which said two portions of the bore are at least partially misaligned for severing a rod held in the bore.

The accompanying drawings, which are incorporated in and form a part of the specification illustrate preferred embodiments of the present invention, and together with the description, serve to explain the principles of the invention. In the drawings:

BRIEF DESCRIPTION OF THE DRAWINGS

FIG. 1 is a side elevational view of the rod cutter.
FIG. 2 is a top plan view thereof.
FIG. 3 is an enlarged side elevational view of the cutting head, partially broken away to show internal construction.
FIG. 4 is a cross-sectional view taken along the planes of line 4—4 of FIG. 3.
FIG. 5 is an end elevational view of a typical rod end cut in the cutter, showing characteristic surface features.

BEST MODE FOR CARRYING OUT THE INVENTION

The surgical rod cutter 10 as shown in the drawings is a bench mounted tool that is especially adapted to cleanly sever stainless steel implant rod used for spinal surgery, which rod typically is referred to as surgical 316-L implant rod. This rod must be custom fitted to the patient during the operation. Consequently, the rod is cut in the operating room at the time it is known how long the rod must be. However, the rod is constructed of extremely hard metal and is difficult to cut. As a result, large bolt cutters have been the tool of choice, largely because no other suitable tool was adaptable to the job. While such bolt cutters are suitable for performing the minimum required function of severing the rod, it has been unfortunate that the cut end of the rod is rough and pointed, which is a result of the tearing action of the bolt cutter. The rod cutter 10 differs from such a bolt cutter in its operation, in that the rod cutter shears and twists the rod, leaving a smooth, burr free surface at the cut end. In addition, the rod cutter confines both ends of the cut rod so that they do not fly free after the cut. The cutter is constructed of a base means for supporting the cutter on a bench or like surface, a tool head means for shearing the rod when the tool is operated, and a handle means for operating the tool head. This construction is particularly desirable in view of the difficulty in cutting a surgical steel workpiece with a hand tool. In particular, by supporting the tool on a bench, the base means enables the tool operator to use both hands and such body weight as may be required to move the handle. It has been found that the operator can cut rod successfully with this tool without using a great deal of strength, in sharp contrast to the typical practice when a bolt cutter is employed.

The base means may be a stable platform that is formed of an elongated beam 12, with one or more lateral stabilizers attached. For example, a front base plate 14 and a rear base plate 16 are shown in FIGS. 1 and 2 to be mounted transversely to the beam 12, each near an opposite end. Proportionately, the base plates each are preferred to have an overall width of at least about one-third the length of the beam and each may have a length of about one-fifth the length of the beam. Variations in the design might employ a still longer base plates, or a single base plate extending for substantially the full length of the beam.

With reference especially to FIGS. 3 and 4, the tool head means is provided with a tool body or shell 18 attached to the base means. For example, the body is attached to the base means by any suitable fasteners, such as by a pair of screws extending through beam 12, which permits disassembly of the tool as required. The body itself is substantially cylindrical and is mounted to the base with the central axis of the cylinder carried transversely to the longitudinal axis of the base. The elongated beam 12 may define a dished seat 20 over the rear base plate 16 in order to provide a stable reception area for the tool body.

As best shown in FIG. 4, the tool body or shell 18 defines an inner chamber in the shape of a hollow cylinder having open ends. At one open end of the cylinder is a radially inwardly extending lip 22, which serves as a bearing retainer. In addition, an axially extending flange 24 is defined at the opposite open end of the cylinder. The flange is preferred to be internally threaded for receipt of a cap 26. Between the flange and lip is defined a substantial central, hollow cavity or volume of the body, which hollow volume has a diameter of, for example, about eighty percent of the overall diameter of the cylindrical body or shell. This central cavity or volume may have an axial dimension of about sixty percent of the length of the cylinder's central axis. A first bore defining member, which may be a cap 26, closes one end of the cylindrical body by engaging the threaded flange 24 while the cap, itself, covers the axial end of the flange having an annular lip 28.

Inside the cylindrical body 18 is mounted a bearing means such as a needle or roller bearing 30. The inside, circumferential wall surfaces of the body serve as a bearing race, while the lip 22 and cap 28 act as axial retainers of this bearing. A second bore defining member, which may be a rotatable core or hub 32, is retained within the center of the bearing 30 for rotation upon the bearing. The core is sized to be received in the body 18 through the relatively wider opening of the flanged end 24. A relatively broad end of the core 32 fits within the center of bearing 30 while being of sufficient diameter to be retained against passage through the relatively smaller opening of the lipped end of the body. At the same time, a relatively narrower end 36 of the core extends axially of the body 18 through the lipped end of the body for eventual attachment to the handle means.

The bearing 30 permits free rotation of the core within the body. One or more matching, coaxial, rod-receiving and retaining bores 38 are formed through cap 26 and core 32. Each pair of matching bores is of a single preselected diameter, although if multiple pairs of bores are used, each pair may be of a different diameter from the others. The bores are of diameters approximately corresponding to a predetermined diameter suitable to receive one of the several sizes of rod workpieces with which the tool is intended for use. Typical rod diameters are one-quarter inch, three-sixteenths inch, and seven millimeters. Typically, two or three matching pairs of such respectively differently sized bores are formed in the cap and core. Each is located as close as possible to the axis of rotation between the cap and core, which may be coaxial with the central axis of the cylinder. Importantly, each bore is laterally offset from that axis. The preferred closeness is within one diameter of the bore to the axis of rotation between the cap and core. This axis also may be referred to as the central pivot axis of the tool head. Notably, because of the circumferential position of the roller bearing 30, the core 32 is does not require the physical presence of a central, axial pivot pin on which to rotate. Thus, the bores 38 can be very close to the central, pivot axis of the core and cap. Primarily, their closeness is limited by the need to retain adequate wall strengths between adjacent bores, so that the core and cap can be rotated relatively to each other to sever rods without causing failure of the bore walls.

Rotation between the core and cap is controlled by the handle means. Two elongated handle sections may define the full handle, with a first, front handle section 40 being attached to end portion 36 of the core where it extends from the body. The attachment between front handle section 40 and core 32 is by a mechanically non-rotatable means. For example, the attached end of handle 40 may define a circular hole sized to snugly receive core end 36. At a point along the annular boundary between the handle and core, a dowel pin 42 is commonly received in a shared bore, thus preventing any relative rotation between the two pieces.

Rotation between the core 32 and cap 26 further is limited by a means for limiting the arc of movement of the handle 40. With reference to FIG. 3, for example, one such means is shown to be a groove 44 formed in the circumferential surface of the handle 40. A stop pin 46 is fixedly mounted to base 12 and extends upwardly from the base and into the groove. Interference with the pin prevents handle movement beyond the arc of the groove. A groove of about seventy degrees of arc is preferred, since handle movement over this arc has proven to be adequate to sever rods.

The handle means is provided with a second, rear section 48 that is movably connected to the front section 40. For example, the two sections may be pivotally connected, such as by a pivot pin 50. The two handle sections can be fastened by a locking means into relatively extended position for use. For this purpose, a spring latch 52 is attached to one section of the handle. A fastener such as a screw or rivet 54 can be used to permanently connect one end of the latch to the forward section of the handle near the junction of the two handle portions. The opposite end of the latch carries a latching pin 56 that extends through the first handle section for engagement with a suitable receptacle 58 in the second handle section.

The solid line position of handle section 48 near the top of FIG. 1 shows the handle locked in extended position when the pin 56 engages handle section 48. A dished notch or scallop 60 is located on handle section 48 and contributes to smooth pivotal movement of handle section 48 as it moves from the dashed line position to the latched, solid line position in this figure. This notch provides a camming surface that, while the two handle portions are coming into alignment, gradually presses back pin 56. When the two portions are fully aligned, the receptacle 58 has been moved under pin 56, which then automatically snaps into locking engagement with it. The latch lever 52 is provided with a finger engageable tab 62 for withdrawing the pin 56 from receptacle 58 when the handle sections are to be folded into non-extended position.

One requirement of equipment used in surgery is that it can be sterilized. The extended handle sections are quite long, for example twenty-six inches, which is larger than many autoclave chambers. Therefore, the handle has been made to be foldable to a reduced overall length, as described above and shown in FIG. 2. Despite the need to fold the handle, the presence of a grip member 64 is desirable at the free end of handle section 48. When the tool is in use, this grip spreads the pressure of operating the tool over a broad area of the user's hand. So that the handle sections can be pivoted in side-by-side relationship on pin 50, the enlarged grip member is offset entirely to one side of handle portion 48, opposite from handle portion 40. With the handle so positioned, the two sections of the handle are able to be folded in closely juxtaposed relationship.

The bores through cap 26 and core 32 are matching, or coaxially aligned, only in one position of relative rotation between these members. At this rotational point of alignment, a rod of suitable size can be pushed through a matching bore to whatever degree is desired. An index mark 66 is provided on the surface of the tool head as an aid to the user in locating the rod in order to produce the finished cut rod of desired length. This mark shows the depth of the opposed faces of the cap and core in the matching bores. The solid line handle position of FIG. 1 shows an approximation of how high the handle is raised when the matching bores align. The handle is preferred to be raised from horizontal to about sixty degrees. With the handle at approximately this angle, the operator can apply his strength and weight when starting the cutting operation. A cutting load on the handle of approximately seventy pounds is all that is required.

As the cutting operation proceeds, the handle is moved progressively downwardly, from the solid line position of FIG. 1 to the lower broken line position, as indicated by the arrow. Because the bores 38 are very close to the common axis or rotation of the cap and core, the bores do not fully misalign even at the completion of the stroke, which may be sixty to seventy degrees of arc from the beginning point. More specifically, the matching bores continue to overlap by about from five percent to thirty percent of their cross sections. Despite this incomplete misalignment of the bore portions, the steel rod can be completely sheared. It has been observed that the cut faces of the rods bear a highly distinctive pattern, which is reproduced in FIG. 5. Here, the rod face 70 shows a shear area 72, bearing curved striations. This area was cut by the opposite offsetting motions within the tool head as the two matching portions of the selected bore were moved in opposite directions. In addition, the rod face shows a second, oval or crescent shaped area 74 that has snapped smoothly, leaving no burr on the edge of the cut face of the rod. This pattern shows that a torque or wringing action has been applied to the rod while the offset shearing was being accomplished. Thus, by a combination of shearing action on one hand, and twisting, wrenching, or wringing action on the other, the rod is severed cleanly and without requiring the complete offset of the cutting bore. If any burr is formed at the rod end during cutting, this burr is near the middle of the rod end face and is not at the outside edge, where is would be objectionable.

A residual overlap in the bores 38 even at the extreme limit of handle movement is the result of the close proximity of the matching bores to the axis of rotation between the cap and core. Each pair of matching bores is located within one diameter of the bore to the axis of rotation. This closeness of the bores to that axis is achieved by elimination of a pivot pin at the common center. Thus, by concentrating the location of the cutting bores only slightly laterally offset from the central pivot axis or axis of rotation, a total of three such cutting bores can be placed around the pivot axis of each tool head.

In some instances the rod will not be fully severed at the conclusion of the downstroke. When this occurs, the cut is completed by raising the handle through a short arc. Because the metal in the rod has been partially shorn by offsetting motion in a first direction, this reverse offsetting motion quickly completes the task, still without creating objectionable burrs. The locking latch pin between the pivoted handle sections assures that the handle can be raised without unintentional folding.

When the rod has been cut fully, the two cut segments still are retained in the tool head. Each bore portion generally will retain the cut end against flying away or dropping.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

I claim:
1. A rod cutter, comprising:
   a base means for supporting the cutter, in use, against a underlying surface;
   a tool head means for, in use, shearing a rod when said tool head means is operated, carried by said base means, wherein the tool head means comprises:
   a hollow cylindrical body having a longitudinal central axis,
   an end cap closing one end of said body and maintained in relatively fixed position with respect to the body,
   a core means carried at least partially within the body for rotation on said central axis of the body, and
   an annular bearing carried between the body and the core means;
   wherein:
      said bearing supports the core means for rotation with respect to said end cap;
      the core means and the end cap mutually define at least one bore having first and second bore portions located, respectively, in the core means and in the end cap;
      the first and second bore portions are laterally offset from the central axis of the body; and
      the core means and the end cap are relatively movable with respect to each other between a first and a second predetermined position of rotation about the central axis, wherein while in said first position of rotation the first and second bore portions are coaxially aligned and while in said second position of rotation the first and second bore portions are at least partially misaligned for, in use, severing a rod held in the bore;
   a handle means for operating the tool head means by moving through an arc relatively to the base means, wherein said handle means is connected to the core means and rotatably moves the core means with respect to the end cap through an arc between at least the first position and the second position; and
   the handle means is formed of at least a latching means, a first elongated handle section, and a second elongated handle section;
   wherein:
      the first and second handle sections are movably joined together near one end of each, such that the sections are moveable between a longitudi- nally extended position and a non-extended position;

the first handle section is attached at its end opposite from the second section to the core means;

the latching means is carried by at least one of the handle sections for releasably locking the first and second handle sections in the longitudinally extended position;

the second handle section defines a handle grip located at the end of the second handle section opposite from the first handle section when in the longitudinally extended position; and said handle grip is offset substantially entirely to one side of the second handle portion, allowing the handle portions to be positioned in the non-extended position without interference by the grip.

2. The rod cutter of claim 1, further comprising:

a pivot pin joining together said first and said second handle sections near one end of each, such that the sections are pivotable between said longitudinally extended position and a folded, mutually juxtaposed position;

wherein said handle grip is offset to a side of the second section opposite the first handle section, relative to the positions of the handle sections when in said juxtaposed position.

3. The rod cutter of claim 1, further comprising a means for limiting the arc of movement of said first handle section with respect to the base means to approximately no more than seventy degrees.

4. The rod cutter of claim 3, wherein said means for limiting the arc of movement of said first handle section comprises:

a stop pin carried by said base means; and wherein said handle means defines a groove of predetermined length on a surface thereof receiving said stop pin and limiting movement of the first handle section by interference between the stop pin and an end of the groove.

* * * * *